United States Patent [19]

Iwataki et al.

[11] Patent Number: 4,504,305
[45] Date of Patent: Mar. 12, 1985

[54] CYCLOHEXENONE DERIVATIVES, PREPARATION AND HERBICIDAL USE

[75] Inventors: Isao Iwataki; Akira Nakayama; Minoru Kaeriyama; Hisao Ishikawa; Hideo Hosaka; Kenichi Kohara, all of Kanagawa, Japan

[73] Assignee: Nippon Soda Co., Ltd., Tokyo, Japan

[21] Appl. No.: 453,498

[22] Filed: Dec. 27, 1982

[30] Foreign Application Priority Data

Feb. 24, 1982 [JP] Japan .................................. 57-28443
May 26, 1982 [JP] Japan .................................. 57-88044
May 26, 1982 [JP] Japan .................................. 57-88045

[51] Int. Cl.³ .................... A01N 31/00; A01N 38/08; A01N 47/28; A01N 37/18
[52] U.S. Cl. .................... 71/98; 260/455 R; 260/453 RW; 560/35; 562/440; 564/84; 564/184; 564/194; 564/95; 564/98; 564/163; 564/50; 564/27; 71/100; 71/111; 71/103; 71/99; 71/118; 71/120
[58] Field of Search .................... 260/455 R; 560/35; 562/440; 564/100, 84, 85, 80, 49, 183, 184; 71/100, 111, 98, 103, 99, 119, 118

[56] References Cited

U.S. PATENT DOCUMENTS 3,574,737  4/1971  Grigat et al. .................... 560/35

OTHER PUBLICATIONS

Iwataki, "Advances in Pesticide Science", Pergamon Press, Oxford and New York, 1979.

Primary Examiner—Henry R. Jiles
Assistant Examiner—Robert C. Whittenbaugh
Attorney, Agent, or Firm—George B. Oujevolk

[57] ABSTRACT

A compound having the general formula

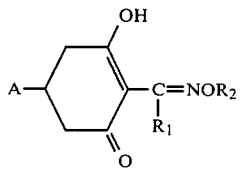

wherein
$R_1$ is alkyl having 1-3 carbon atoms;
$R_2$ is alkyl having 1-3 carbon atoms, allyl, propargyl or haloalkenyl; and
A is selected from the group consisting of

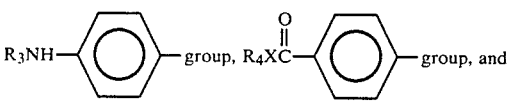

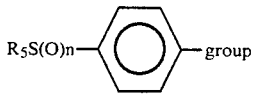

wherein $R_3$ is —$SO_2R_6$ group,

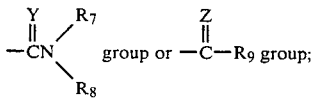

$R_4$ is hydrogen, alkyl having 1-6 carbon atoms; phenyl or halophenyl; $R_5$ is alkyl having 1-3 carbon atoms; X is oxygen or sulfur; and n is 0 or 1; wherein $R_6$ is alkyl having 1-6 carbon atoms, haloalkyl having 1-6 carbon atoms or propenyl; $R_7$ is hydrogen or alkyl having 1-4 carbon atoms; $R_8$ is hydrogen, alkyl having 1-6 carbon atoms; propenyl or methoxy; $R_9$ is hydrogen, alkyl having 1-8 carbon atoms, haloalkyl having 1-3 carbon atoms, alkoxy having 1-6 carbon atoms, propenyl or phenyl substituted with methyl; and Y and Z are oxygen or sulfur; and a metal salt or a quaternary ammonium salt of a compound defined herein above.

The compound is useful as a herbicide.

15 Claims, No Drawings

CYCLOHEXENONE DERIVATIVES, PREPARATION AND HERBICIDAL USE

The present invention relates to cyclohexenone derivatives, to a process for the preparation thereof and their uses as selective herbicides.

According to the present invention, there are provided a compound of the formula

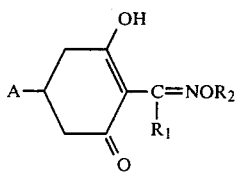

wherein
$R_1$ is alkyl having 1-3 carbon atoms;
$R_2$ is alkyl having 1-3 carbon atoms, alkyl, propargyl or haloalkenyl; and
A is selected from the group consisting of

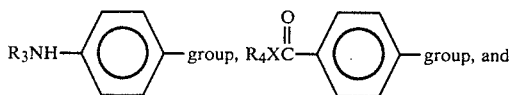

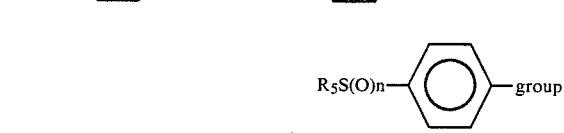

wherein $R_3$ is —$SO_2R_6$ group,

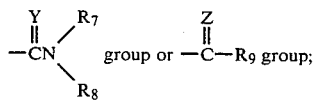

$R_4$ is hydrogen, alkyl having 1-6 carbon atoms, phenyl or halophenyl; $R_5$ is alkyl having 1-3 carbon atoms; X is oxygen or sulfur; and n is 0 or 1;
wherein
$R_6$ is alkyl having 1-6 carbon atoms, haloalkyl having 1-6 carbon atoms or propenyl;
$R_7$ is hydrogen or alkyl having 1-4 carbon atoms;
$R_8$ is hydrogen, alkyl having 1-6 carbon atoms, propenyl or methoxy;
$R_9$ is hydrogen, alkyl having 1-8 carbon atoms, haloalkyl having 1-3 carbon atoms, alkoxy having 1-6 carbon atoms, propenyl or phenyl substituted with methyl; and Y and Z are oxygen or sulfur; and a metal salt or a quaternary ammonium salt of a compound defined herein above.

It is disclosed in U.S. Pat. Nos. 3,950,420 and 4,011,256 that some cyclohexenone derivatives give excellent control of grassy weeds. The above compounds also cause heavy damage to gramineous crops. Thus we conducted further investigation to find out new compounds which provide no phytotoxicity against gramineous crops. As the result, we found that 2-[(1-ethoxyimino)-propyl]-5-(substituted phenyl)-3-hydroxy-2-cyclohexene-1-one showed a slightly weak action on wheat. [Advances in Pesticide Science Part 2 235 (1979)]. They are relatively selective at the lower stage of grass weeds and wheat in post-emergence treatment. However, the bigger they grow, the higher the dose is needed. Thus, using higher rate of active ingredient, more herbicidal activity against grassy weeds is obtained and at the same time heavier damage is caused on wheat. On the other hand, decreasing the dosage to the rate which gives no phytotoxicity toward wheat, herbicidal activity is less effective. Thus the optimum dose range for giving a good selectivity is limited. To improve these adverse properties and to obtain more active and more selective compounds we conducted further studies.

We have found that the compounds having the formula [I] show higher activity and/or remarkably higher selectivity against gramineous crops such as corn, wheat, barley and rice compared with the known compounds. That is; the compounds having

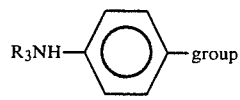

(wherein $R_3$ is as previously defined) show only a slightly weak action toward gramineous crops such as corn, wheat and barley, especially corn, and a high herbicidal activity on grassy weeds, especially wild oat.

The compounds having

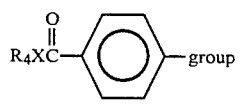

(wherein $R_4$ and X are as previously defined) show not only higher activity on grassy weeds but also higher selectivity between wheat and wild oat.

Further, the compounds having

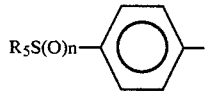

(wherein $R_5$ and n are as previously defined) increase significantly in activity against grass weeds compared with the known compounds containing phenyl substituted with methoxy or methylsulfonyl, though both compounds are almost equal selectivity.

All the compounds of this invention are active against gramineous weeds in both pre- and post-emergence treatment. Higher activities can be expected in post-emergence treatment than in pre-emergence treatment.

The compounds of this invention can be prepared in accordance with the following equation:

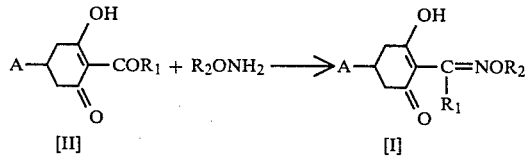

wherein $R_1$, $R_2$ and A are as previously defined.

The above reaction can be conducted in an inert solvent.

As an inert solvent, methanol, ethanol, diethyl ether, benzene, toluene and chloroform may be used.

The reaction temperature may be from −10° C. to the boiling point of the reaction solution, preferably from 10° to 60° C., and the reaction may be carried out from half an hour to several hours or longer.

After the reaction has been completed, the solvent is, if necessary, removed and the reaction mixture is then extracted with an alkaline solution. The solution is acidified with hydrochloric acid and the crude product is isolated from the acid mixture by extraction or by filtration.

If the product is crystalline, the crude product can be purified by recrystallization, and if the product is an only substance, the crude product can be purified by distillation or column chromatography.

A chemical formula for the resulting purified compound can be assigned by means of an elemental analysis, NMR spectrum, MASS spectrum and IR spectrum.

The sodium and potassium salts may be prepared by treating a compound of formula [I] with sodium or potassium hydroxide in an aqueous solution or in an organic solvent such as acetone, methanol, ethanol or dimethylformamide. The salts may be isolated by filtration or by evaporation of the resulting solution.

The calcium, barium manganese, copper, zinc, nickel, cobalt, iron and silver salts may be prepared from the sodium or potassium salt by treatment with the appropriate inorganic metal salt, e.g. calcium chloride, barium chloride, copper sulfate, zinc chloride, nickel chloride and cobalt nitrate.

The calcium salt may also be prepared by treating a compound of the formula [I] with calcium hydroxide.

Some metal salts produced by above-mentioned process may undergo a chemical change or decomposition at a high temperature, and therefore not show a clear melting point. By applying infrared absorption spectroscopy to the starting material and reaction product, the formation of the metal salt is evidenced by transference of absorption bands and a change of absorption intensity. Thus, the starting material having the formula [I] has the absorption due to the carbonyl group at wavelengths 1605 cm$^{-1}$ and 1655 cm$^{-1}$, whereas the corresponding metal salt shows the absorption at longer wavelengths.

Further, an anion such as OH may be simultaneously coordinated with a metal atom of some metal salts mentioned above.

The structure of the metal salt may be shown as follows:

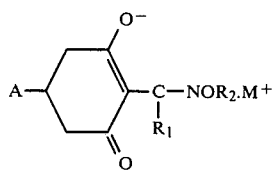

wherein $M^+$ is metal ion such as $Na^+$, $\frac{1}{2}Ca^{2+}$ or $\frac{1}{2}Cu^{2+}$.

Ammonium salts of this invention may be shown as same as the metal salts, namely,

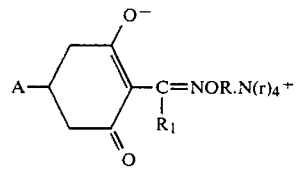

wherein $N^+(r)_4$ is quaternary ammonium ion and r is same or different substituent selected from alkyl and benzil. The ammonium salt can be prepared by the reaction of the compound of the formula [I] with ammonium hydroxide [$N(r)_4OH$] in the same manner as in the preparation of sodium salt.

It is expected that the compounds represented by the formula [I] exist in the following tautomeric forms:

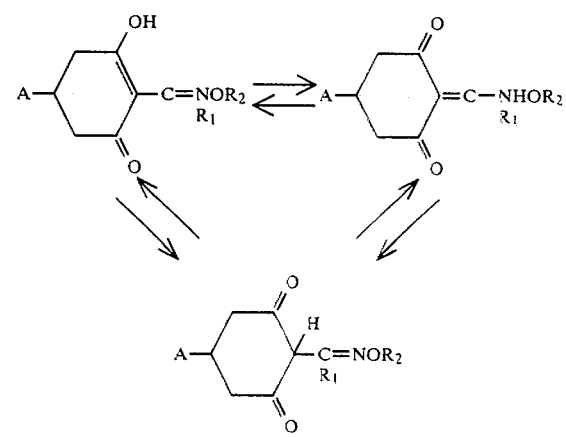

The starting material of the formula [II] can be prepared in accordance with the following equation:

(1) In case of the compounds having

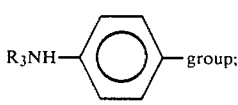

group;

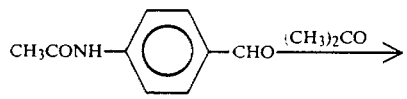

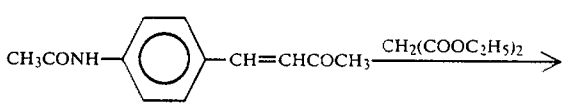

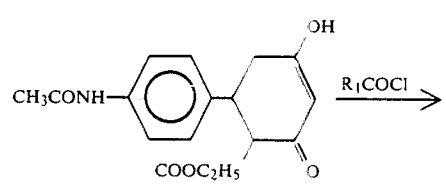

-continued
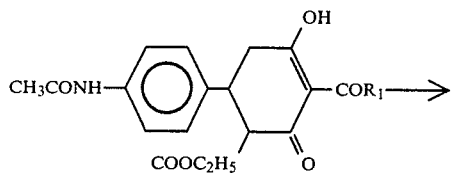
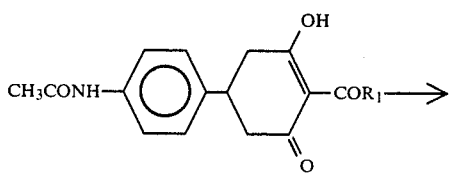
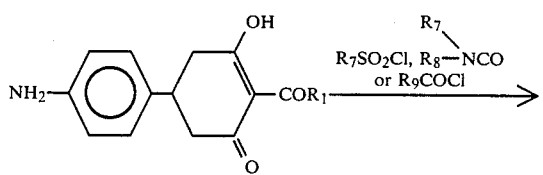
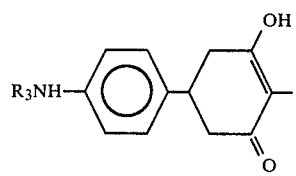
(2) In case of the compounds having
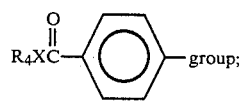group;
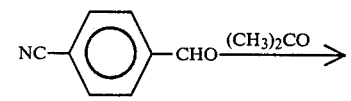
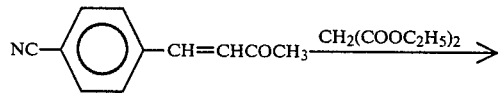
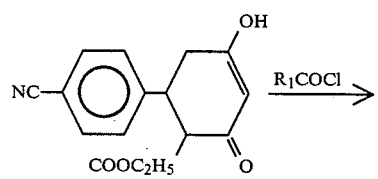
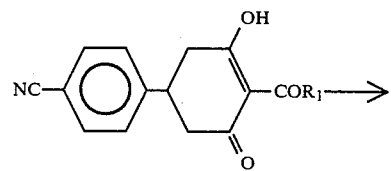
-continued
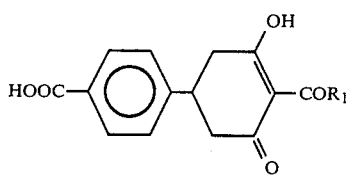
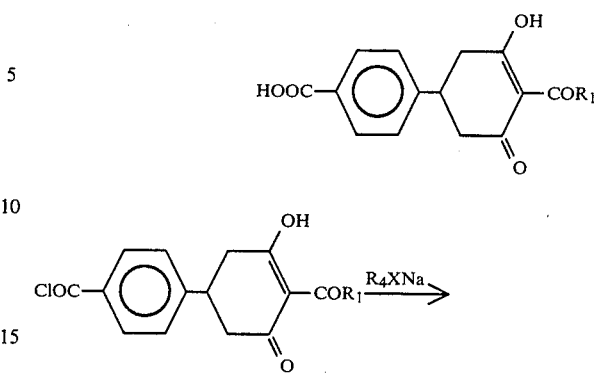
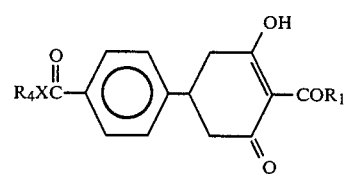
(3) In case of the compounds having
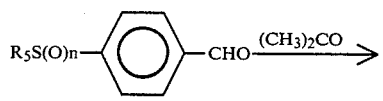group;
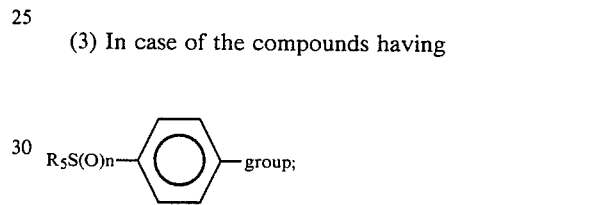
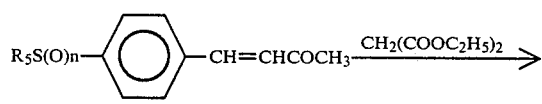
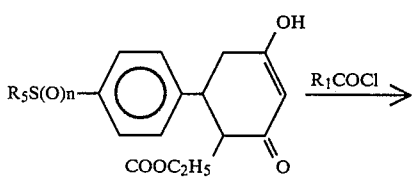
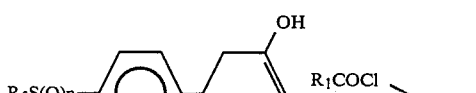
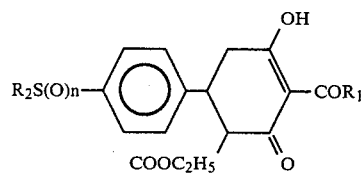
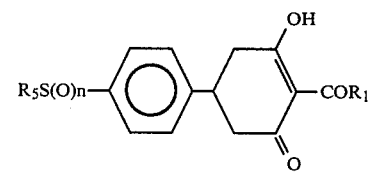
The following Examples illustrate the invention:

EXAMPLE 1:
2-[1-(ethoxyimino)propyl]-3-hydroxy-5-(4-methanesulfonamidophenyl)-2-cyclohexen-1-one Into 10 ml of tetrahydrofuran was dissolved 1.5 g of 3-hydroxy-5-(4-methanesulfonamidophenyl)-2-propionyl-2-cyclohexen-1-one and to the solution was added 0.5 g of ethoxyamine. The mixture was kept at room temperature for 15 hours and poured into ice water. And then the mixture was acidified with hydrochloric acid and it was extracted with chloroform. The chloroform solution was washed with water and extracted with 15 ml of an aqueous solution containing 5% of sodium hydroxide. The solution was acidified with hydrochloric acid and the crystal sedimented was extracted with chloroform and the solution was washed with water and it was dried with magnesium sulfate. Then, it was distilled off under a reduced pressure and thus, 1.4 g of the desired compound was obtained. It was in the form of colorless crystals having a melting point of 115°–116° C.

EXAMPLE 2:
2-[1-(allyloxyimino)propyl]-5-(4-methanesulfonamidophenyl)-3-hydroxy-2-cyclohexen-1-one Into 10 ml of tetrahydrofuran was dissolved 1.0 g of 5-(4-methanesulfonamidophenyl)-3-hydroxy-2-propionyl-2-cyclohexen-1-one and to the solution was added 0.5 g of allyoxyamine. The mixture was kept at room temperature for 15 hours and then it was treated with similar to Example 1. Thus, 0.8 g of the desired compound was obtained. It was in the form of colorless crystals having a melting point of 134°–135° C.

EXAMPLE 3:
2-[1-(methoxyimino)propyl]-5-(4-methanesulfonamidophenyl)-3-hydroxy-2-cyclohexen-1-one Into 10 ml of tetrahydrofuran was dissolved 1.2 g of 3-hydroxy-5-(4-methanesulfonamidophenyl)-2-propionyl-2-cyclohexen-1-one and to the solution were added 0.6 g of methoxyamine hydrocholorate salt and 1.4 g of methanol containing 28% of sodium methylate. Then, the mixture was kept for 15 hours at room temperature and an insoluble material was filtered off from it and the resulting filtrate solution was concentrated under reduced pressure. Its residue was dissolved in chloroform and the solution was washed with a dilute hydrochloric acid solution and water, and it was dried with anhydrous magnesium sulfate. The chloroform was distilled off from it under a reduced pressure and ethyl ether was add in it. Thus, the crystal sedimented is collected with a filtering step and 1.2 g of the desired compound as colorless crystals having a melting point of 150°–151° C. was obtained.

EXAMPLE 4:
2-[1-(3-chloroallyloxyimino)propyl]-3-hydroxy-5-(4-methanesulfonamidophenyl)-2-cyclohexen-1-one Into 40 ml of mixture solvent of ethanol-chloroform (1:1) was dissolved 2 g of 3-hydroxy-5-(4-methanesulfonamidophenyl)-2-propionyl-2-cyclohexen-1-one and to the solution was added 10 ml of ethanol containing 10% of 3-chloroallyloxyamine at room temperature. The mixture was kept for 3 hours and it was poured into ice water. The mixture was acidified with hydrochloric acid and the oil separated was extracted with chloroform. The chloroform solution was dried with anhydrous magnesium sulfate and the chloroform was removed from it under reduced pressure and 1.5 g of the desired crude compound was obtained. It was purified by column chromatography and trans-cis mixture which was pale pink crystal having a melting point of 125°–127° C. was obtained.

EXAMPLE 5:
2-[1-(ethoxyimino)propyl]-3-hydroxy-5-[4-(3,3-dimethylurado)phenyl]-2-cyclohexen-1-one Into 6 ml of ethanol was dissolved 1.0 g of 3-hydroxy-5-[4-(3,3-dimethylurado)phenyl]-2-propionyl-2-cyclohexen-1-one and to the solution was added 0.5 g of ethoxyamine. The mixture was kept for 3 hours at room temperature and it was poured into ice water. Then, the mixture was acidified with a dilute hydrochloric acid solution and it was extracted with chloroform. The chloroform solution was washed with water and extracted with 10 ml of aqueous solution containing 5% of sodium hydroxide. To the alkaline solution was add a dilute hydrochloric acid solution and the crystal sedimented was extracted with chloroform. The chloroform solution was washed with water and dried with anhydrous magnesium sulfate. The chloroform was distilled off from it under a reduced pressure and ethyl ether was added in the residue. Thus, the crystal sedimented was collected with a filtering step and 0.9 g of the desired compound which were in the form of colorless crystals having a melting point of 77°–79° C. was obtained.

EXAMPLE 6:
2-[1-(ethoxyimino)propyl]-5-{4-[3-(ethyl)thioureido]phenyl}-3-hydroxy-2-cyclohexen-1-one Into 10 ml of chloroform was dissolved 1.4 g of 5-{4-[3-(ethyl)thioureido]phenyl}-3-hydroxy-2-propionyl-2-cyclohexen-1-one and to the solution was added 1.0 g of ethoxyamine. The mixture was kept for 15 hours at room temperature and the reacting mixture was washed with a dilute hydrochloric acid solution and water. The solution was dried with anhydrous magnesium sulfate and the chloroform was distilled off from it under reduced pressure and 1.4 g of the desired compound was obtained. It was in the form of colorless crystals having a decomposition point of 116°–118° C.

EXAMPLE 7:
5-(4-acetamidophenyl)-2-[1-(ethoxyimino)propyl]-3-hydroxy-2-cyclohexen-1-one Into 10 ml of tetrahydrofuran was dissolved 2.0 g of 5-(4-acetamidophenyl)-2-propionyl-3-hydroxy-2-cyclohexen-1-one and to the solution was added 1.0 g of aqueous solution containing 50% of ethoxyamine. The mixture was kept for 15 hours at room temperature and it was poured into ice water and the crystal sedimented was collected with a filtering step. The crystal was dissolved in 20 ml of chloroform and the solution was washed with water and extracted with 15 ml of aqueous solution containing 5% of sodium hydroxide. To the alkaline solution was added a dilute hydrochloric acid solution and the crystal sedimented was extracted with chloroform. The solution was washed with water and dried with anhydrous magnesium sulfate and the chloroform was distilled off from it under reduced pressure. Thus 1.4 g of the desired compound was obtained. It was in the form of pale yellow crystals having a melting point of 135°–136° C.

EXAMPLE 8:
2-[1-(ethoxyimino)propyl]-5-(4-formamidophenyl)-3-hydroxy-2-cyclohexen-1-one Into 25 ml of chloroform was dissolved 1.3 g of 5-(4-formamidophenyl)-3-hydroxy-2-propionyl-2-cyclohexen-1-one and to the solution was added 1.0 g of ethoxyamine and 5 ml og ethanol. The mixture was kept for 3 hours in a water bath having 40° C. and the reacting solution was washed with a dilute hydrochoric acid solution and water. The solution was extracted with 15 ml of aqueous solution containing 5% of sodium hydroxide and to the alkaline solution was added a dilute hydrochloric acid solution and the crystal sedimented was extracted with chloroform. The solution was washed with water and to the solution was added anhydrous magnesium sulfate and a small amount of active carbon. And then, the mixture was agitated and filtered and the filtrate solution was concentrated. Ethyl ether was added in the residue and the crystal sedimented was collected with a filtering step and 1.0 g of desired compound was obtained. It was in the form of colorless crystals having a melting point of 111°–113.5° C.

EXAMPLE 9:
2-[1-(ethoxyimino)propyl]-5-[4-(2-methylbenzamido)-phenyl]-3-hydroxy-2-cyclohexen-1-one Into 30 ml of chloroform was dissolved 1.6 g of 5-[4-(2-methylbenzamido)phenyl]-2-propionyl-3-hydroxy-2-cyclohexen-1-one and to the solution was added 0.4 g of ethoxyamine. The mixture was kept for 15 hours at 40° C. and the reacting solution was washed with water and a surplus amount of ethoxyamine was removed from it. After dried, the chloroform was distilled off from it and ethyl ether was added in the residue. The crystal sedimented was collected with a filtering step and 1.0 g of desired compound was obtained. It was in the form of colorless crystals having a melting point of 139°–140° C.

EXAMPLE 10:
2-[1-(ethoxyimino)propyl]-5-[4-(methoxycarbonylamino)phenyl]-3-hydroxy-2-cyclohexen-1-one Into 30 ml of chloroform was dissolved 1.8 g of 5-[4-(methoxycarbonylamino)phenyl]-2-propionyl-3-hydroxy-2-cyclohexen-1-one and to the solution was added 0.5 g of ethoxyamine. The mixture was agitated for 15 hours at 40° C. and the chloroform containing produced water and a surplus amount of ethoxyamine was distilled off from it under a reduced pressure. And then, the ethyl ether was added in the residue and the crystal sedimented was collected with a filtering step and 1.2 g of desired compound was obtained. It was in the form of colorless crystals having a melting point of 160°–161° C.

EXAMPLE 11: Sodium
2-[1-(ethoxyimino)propyl]-5-(4-methansulfonamidephenyl)-3-oxo-1-cyclohexenolate Into 10 ml of methanol was dissolved 1.9 g of 2-[1-(ethoxyimino)propyl]-5-(4-methansulfonamidephenyl)-3-hydroxy-2-cyclohexen-1-one and to the methanol solution was added 20 ml of methanol containing 0.27 g of sodium methylate. Then, the solvent was removed under a reduced pressure and the residue was recrystallized with acetonitrile. Thus, 1.8 g of the desired compound which was a colorless crystal having a decomposition point of 165°–170° C. was obtained.

EXAMPLE 12: Calcium
2-[1-(ethoxyimino)propyl]-5-(4-methanesulfonamidophenyl)-3-oxo-1-cyclohexenolate Into 20 ml of an aqueous solution containing 2% of sodium hydroxide was dissolved 1.9 g of 2-[1-(ethoxyimino)propyl]-5-(4-methanesulfonamidophenyl)-3-hydroxy-2-cyclohexen-1-one and to the solution was added 3 cc of an aqueous solution containing 10% of calcium chloride at room temperature. The water was removed under a reduced pressure and the residue was dissolved in ethanol and an insoluble sodium chloride was separated with a filtering step. The ethanol was distilled off under reduced pressure and 1.5 g of white powder having a melting point of 250° C. or more was obtained.

EXAMPLE 13: Benziltrimethylammonium
2-[1-(ethoxyimino)propyl]-5-(4-butylamidephenyl)-3-oxo-1-cyclohexenolate Into 30 ml of methanol was dissolved 1.9 g of 2-[1-(ethoxyimino)propyl]-5-(4-butylamidephenyl)-3-hydroxy-2-cyclohexen-1-one and to the solution was added 2.2 g of methanol containing 40% of benziltrimethylammonium hydroxide at room temperature. The methanol was distilled off from it under reduced pressure and 2.7 g of colorless hygroscopic crystal having a melting point of 65°–66° C. was obtained.

EXAMPLE 14:
2-[1-(ethoxyimino)propyl]-3-hydroxy-5-(4-methoxycarbonylphenyl)-2-cyclohexen-1-one Into 20 ml of methanol was dissolved 2.5 g of 3-hydroxy-5-(4-methoxycarbonylphenyl)-2-propionyl-2-cyclohexen-1-one and to the solution was added 0.7 g of ethoxyamine. The mixture was kept for 15 hours at room temperature and it was poured into ice water. The crystal sedimented was collected with a filtering step and recrystallized with mixture solvent of methanol-water. Thus, 1.9 g of the desired compound which was in the form of colorless crystals having a melting point of 75°–76° C. was obtained.

EXAMPLE 15:
2-[1-ethoxyimino)butyl]-3-hydroxy-5-[4-(methylthio)-carbonylphenyl]-2-cyclohexen-1-one Into 20 ml of tetrahydrofuran was dissolved 2 g of 2-butyryl-3-hydroxy-5-[4-(methylthio)carbonylphenyl]-2-cyclohexen-1-one and to the solution was added 0.6 g of ethoxyamine. The mixture was kept for 15 hours at room temperature and the solvent was distilled off from it under reduced pressure. Then, the residue was recrystallized with mixture solvent of benzene-ligroin and 1.8 g of colorless desired crystals having a melting point of 75°–77° C. were obtained.

EXAMPLE 16:
3-hydroxy-5-[4-(methylthio)carbonylphenyl]-2-[1-(propargyloxyimino)butyl]-2-cyclohexen-1-one Into 20 ml of tetrahydrofuran was dissolved 2 g of 2-butyryl-3-hydroxy-5-[4-(methylthio)carbonylphenyl]-2-cyclohexen-1-one and to the solution was added 0.7 g of propargyloxyamine. The mixture was kept for 15 hours at room temperature and the solvent was distilled off from it under reduced pressure. Then, the residue was recrystallized with mixture solvent of benzene-ligroin and 1.6 g of colorless desired crystals having a melting point of 95°–96° C. were obtained.

EXAMPLE 17:
2-[1-(allyloxyimino)butyl]-5-[4-(ethylthio)carbonylphenyl]-3-hydroxy-2-cyclohexen-1-one Into 20 ml og tetrahydrofuran was dissolved 2 g of 2-butyryl-5-[4-(ethylthio)carbonylphenyl]-3-hydroxy-2-cyclohexen-1-one and to the solution was added 0.8 g of allyloxyamine. The mixture was kept for 15 hours at room temperature and the solvent was distilled off from it under reduced pressure. Then, the residue was recrystallized with mixture of benzene-ligroin and 0.8 g of colorless objective crystals having a melting point of 72°-75° C. was obtained.

EXAMPLE 18: Sodium
2-[1-(ethoxyimino)propyl]-5-(4-methoxycarbonylphenyl)-3-oxo-1-cyclohexenolate Into 10.8 g of methanol containing 2.5% of sodium methoxide was dissolved 1.7 g of 2-[1-(ethoxyimino)propyl]-3-hydroxy-5-(4-methoxycarbonylphenyl)-2-cyclohexen-1-one and the solvent was removed from it under reduced pressure. Thus, 1.8 g of colorless desired crystals were obtained.

EXAMPLE 19:
2-[1-(ethoxyimino)propyl]-3-hydroxy-5-(4-methylthiophenyl)-2-cyclohexen-1-one Into 20 ml of ethanol was dissolved 2.9 g of 3-hydroxy-5-(4-methylthiophenyl)-2-propionyl-2-cyclohexen-1-one and to the solution was added 0.8 g of ethoxyamine. The mixture was kept for 15 hours at room temperature and it was poured into ice water. The crystal sedimented was collected with a filtering step and recrystallized with methanol. Thus, 3.1 g of colorless objective crystals having a melting point of 83°-84° C. was obtained.

EXAMPLE 20:
2-[1-(allyloxyimino)butyl]-3-hydroxy-5-(4-methylthiophenyl)-2-cyclohexen-1-one Into 20 ml of ethanol was dissolved 1.5 g of 2-butyryl-3-hydroxy-5-(4-methylthiophenyl)-2-cyclohexen-1-one and to the solution was added 0.5 g of allyloxyamine. The mixture was kept for 15 hours at room temperature and it was poured into ice water. The crystal sedimented was collected with a filtering step and recrystallized with methanol. Thus, 1.4 g of colorless objective crystals having a melting point of 72°-74° C. was obtained.

EXAMPLE 21:
2-[1-(ethoxyimino)butyl]-3-hydroxy-5-(4-methylsulfinylphenyl)-2-cyclohexen-1-one Into 20 ml of ethanol was dissolved 1.6 g of 2-butyryl-3-hydroxy-5-(4-methylsulfinylphenyl)-2-cyclohexen-1-one and to the solution was added 0.5 g of ethoxyamine. The mixture was kept for 15 hours at room temperature and it was poured into ice water. The crystal sedimented was collected with a filtering step and recrystallized with methanol. Thus, 1.3 g of colorless objective crystals having a melting point of 72°-74° C. was obtained.

In addition to the above-mentioned compounds, some typical compound are listed in Table 1.

TABLE 1

1-1

| Compound No. | $R_6$ | $R_1$ | $R_2$ | Physical Constant [m.p.] °C. |
|---|---|---|---|---|
| 1 | —$CH_3$ | —$C_2H_5$ | —$C_2H_5$ | [115–116] |
| 2 | —$C_2H_5$ | —$C_2H_5$ | —$C_2H_5$ | [119–120] |
| 3 | —$C_3H_7$ | —$C_2H_5$ | —$C_2H_5$ | [111–112] |
| 4 | —$C_4H_9$ | —$C_2H_5$ | —$C_2H_5$ | [118–119] |
| 5 | —$CH_2Cl$ | —$C_2H_5$ | —$C_2H_5$ | [142–143] |
| 6 | —$CH_3$ | —$C_2H_5$ | —$CH_2CH=CH_2$ | [134–135] |
| 7 | —$CH_3$ | —$C_2H_5$ | —$CH_3$ | [150–151] |
| 8 | —$CH_3$ | —$C_3H_7$ | —$C_2H_5$ | [117–119] |
| 9 | —$CH_3$ | —$C_3H_7$ | —$CH_2CH=CH_2$ | [100–101] |
| 10 | —$CH_2Cl$ | —$C_2H_5$ | —$CH_2CH=CH_2$ | [138–140] |
| 11 | —$CH_2Cl$ | —$C_3H_7$ | —$C_2H_5$ | [102–104] |
| 12 | —$CH_2Cl$ | —$C_3H_7$ | —$CH_2CH=CH_2$ | [134–135] |
| 13 | —$CH_2CH=CH_2$ | —$C_2H_5$ | —$C_2H_5$ | [98–100] |
| 14 | —$CH_2CH=CH_2$ | —$C_2H_5$ | —$CH_2CH=CH_2$ | [90–92] |
| 15 | —$CF_3$ | —$C_2H_5$ | —$C_2H_5$ | [124–126] |
| 16 | —$CH_3$ | —$C_2H_5$ | —$CH_2CH=CHCl$ | [125–127] |

1-2

| Compound No. | Y | $R_7$ | $R_8$ | $R_1$ | $R_2$ | Physical constant [m.p.] °C. |
|---|---|---|---|---|---|---|
| 17 | O | —H | —H | —$C_2H_5$ | —$C_2H_5$ | [115–116] |
| 18 | S | —H | —$C_2H_5$ | —$C_2H_5$ | —$C_2H_5$ | [116–118] |

TABLE 1-continued

| | | | | | | |
|---|---|---|---|---|---|---|
| 19 | O | —CH₃ | —CH₃ | —C₂H₅ | —C₂H₅ | [77–79] dec. |
| 20 | O | —H | —CH₃ | —C₂H₅ | —C₂H₅ | [139–141] |
| 21 | O | —CH₃ | —CH₃ | —C₃H₇ | —C₂H₅ | [132–134] |
| 22 | O | —H | —CH₃ | —C₂H₅ | —CH₂CH=CH₂ | [131–133] |
| 23 | O | —CH₃ | —OCH₃ | —C₂H₅ | —C₂H₅ | [128–131] |
| 24 | S | —H | —CH₃ | —C₂H₅ | —C₂H₅ | [113–114] dec. |
| 25 | S | —H | —CH₂CH=CH₂ | —C₂H₅ | —C₂H₅ | [112–114] dec. |
| 26 | O | —H | —C₂H₅ | —C₂H₅ | —C₂H₅ | [142–144] |
| 27 | O | —C₂H₅ | —C₂H₅ | —C₂H₅ | —C₂H₅ | [92–93] |
| 28 | O | —H | —CH(CH₃)₂ | —C₂H₅ | —C₂H₅ | [144–146] |
| 29 | S | —H | —CH₂CH(CH₃)₂ | —C₂H₅ | —C₂H₅ | [108–110] |
| 30 | O | —H | —C₄H₉ | —C₂H₅ | —C₂H₅ | [143–144] |
| 31 | O | —CH₃ | —CH₃ | —C₂H₅ | —CH₂CH=CH₂ | [63–64] |
| 32 | O | —CH₃ | —CH₃ | —C₃H₇ | —CH₂CH=CH₂ | [80–82] |
| 33 | S | —H | —H | —C₂H₅ | —C₂H₅ | [140–150] dec. |
| 34 | O | —H | —t-C₄H₉ | —C₂H₅ | —C₂H₅ | [133–134] |

1-3

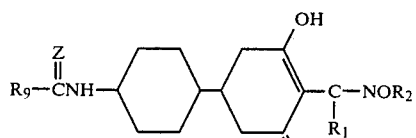

| Compound No | Z | R₉ | R₁ | R₂ | Physical constant [m.p.] °C. |
|---|---|---|---|---|---|
| 35 | O | —CH₃ | —C₂H₅ | —C₂H₅ | [135–136] |
| 36 | O | —C₂H₅ | —C₂H₅ | —C₂H₅ | [147–149] |
| 37 | O | —C₃H₇ | —C₂H₅ | —C₂H₅ | [144–145] |
| 38 | O | —OC₂H₅ | —C₂H₅ | —C₂H₅ | [159–160] |
| 39 | O | CH₃-C₆H₄- 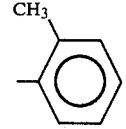 | —C₂H₅ | —C₂H₅ | [139–140] |
| 40 | O | —C₃H₇ | —C₂H₅ | —CH₂CH=CH₂ | [114–116] |
| 41 | S | —OC₂H₅ | —C₂H₅ | —C₂H₅ | [129–132] |
| 42 | O | —CH=CH—CH₃ | —C₂H₅ | —C₂H₅ | [153–154] |
| 43 | O | —H | —C₂H₅ | —C₂H₅ | [111–113.5] |
| 44 | O | —i-C₃H₇ | —C₂H₅ | —C₂H₅ | [131–132] |
| 45 | O | —t-C₄H₉ | —C₂H₅ | —C₂H₅ | [124–125] |
| 46 | O | —CH₃ | —C₂H₅ | —CH₂CH=CH₂ | [127–129] |
| 47 | O | —H | —C₂H₅ | —CH₂CH=CH₂ | [79–81] |
| 48 | O | —CH₂Cl | —C₂H₅ | —C₂H₅ | [177–178] |
| 49 | O | —CH₃ | —C₃H₇ | —C₂H₅ | [130–131] |
| 50 | O | —CH₃ | —C₃H₇ | —CH₂CH=CH₂ | [112–114] |
| 51 | O | —H | —C₃H₇ | —C₂H₅ | [116–117] |
| 52 | O | —H | —C₃H₇ | —CH₂CH=CH₂ | $n_D^{22}$ 1.5988 |
| 53 | O | —(CH₂)₇CH₃ | —C₂H₅ | —C₂H₅ | [104–105] |
| 54 | O | —O(CH₂)₇CH₃ | —C₂H₅ | —C₂H₅ | [87–90] |
| 55 | O | —CF₃ | —C₂H₅ | —C₂H₅ | [187–188] dec. |
| 56 | O | —CF₃ | —C₂H₅ | —CH₂CH=CH₂ | [159–161] |
| 57 | O | CH₃-phenyl | —C₂H₅ | —CH₂CH=CH₂ | [103–105] |
| 58 | O | CH₃-phenyl | —C₃H₇ | —C₂H₅ | [152–153] |

TABLE 1-continued

| No. | | | | | |
|---|---|---|---|---|---|
| 59 | O | 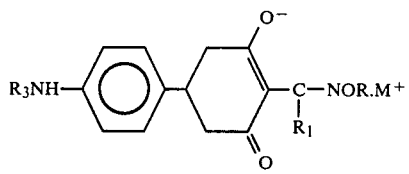CH$_3$ | —C$_3$H$_7$ | —CH$_2$CH=CH$_2$ | [130–131] |
| 60 | O | —OCH$_3$ | —C$_2$H$_5$ | —C$_2$H$_5$ | [160–161] |
| 61 | O | —OCH$_2$CH=CH$_2$ | —C$_2$H$_5$ | —C$_2$H$_5$ | [132–133] |
| 62 | O | —OCH$_3$ | —C$_2$H$_5$ | —CH$_2$CH=CH$_2$ | [113–114] |
| 63 | O | —OCH$_3$ | —C$_3$H$_7$ | —C$_2$H$_5$ | [149–150] |
| 64 | O | —OCH$_3$ | —C$_3$H$_7$ | —CH$_2$CH=CH$_2$ | [119–121] |
| 65 | O | —OC$_2$H$_5$ | —C$_3$H$_7$ | —C$_2$H$_5$ | [142–143] |
| 66 | O | —OC$_2$H$_5$ | —C$_3$H$_7$ | —CH$_2$CH=CH$_2$ | [122–123] |

1-4

$$R_3NH\!-\!\!\bigcirc\!\!-\!\!\underset{\underset{O}{\|}}{\overset{\overset{O^-}{|}}{\bigcirc}}\!\!-\!\!\overset{R_1}{\underset{}{C}}\!\!-\!\!NOR.M^+$$

| Compound No. | R$_3$ | R$_1$ | R$_2$ | M | Physical constant [m.p.] °C. |
|---|---|---|---|---|---|
| 67 | —SO$_2$CH$_3$ | —C$_2$H$_5$ | —C$_2$H$_5$ | Na | [165–170] dec. |
| 68 | —SO$_2$CH$_3$ | —C$_2$H$_5$ | —C$_2$H$_5$ | ½ Ca | [250] up |
| 69 | —COC$_3$H$_7$ | —C$_2$H$_5$ | —C$_2$H$_5$ | Na | [183] dec. |
| 70 | —COC$_3$H$_7$ | —C$_2$H$_5$ | —C$_2$H$_5$ | ½ Sn | [144–146] dec. |
| 71 | —COC$_3$H$_7$ | —C$_2$H$_5$ | —C$_2$H$_5$ | N(CH$_3$)$_3$—CH$_2$—⌬ | [65–66] |
| 72 | —COC$_3$H$_7$ | —C$_2$H$_5$ | —CH$_2$CH=CH$_2$ | Na | [200] up |
| 73 | —SO$_2$CH$_3$ | —C$_3$H$_7$ | —C$_2$H$_5$ | Na | [142–145] |
| 74 | —SO$_2$CH$_3$ | —C$_3$H$_7$ | —CH$_2$CH=CH$_2$ | Na | hygroscopic |
| 75 | —SO$_2$CH$_2$CH=CH$_2$ | —C$_2$H$_5$ | —C$_2$H$_5$ | Na | [85–88] |
| 76 | —CON(CH$_3$)$_2$ | —C$_2$H$_5$ | —C$_2$H$_5$ | Na | [180–182] dec. |
| 77 | —CONHCH$_3$ | —C$_2$H$_5$ | —C$_2$H$_5$ | Na | [183–185] dec. |
| 78 | —CONHCH$_3$ | —C$_2$H$_5$ | —C$_2$H$_5$ | ⅓ Fe | [147–149] dec. |
| 79 | —CONHCH$_3$ | —C$_2$H$_5$ | —C$_2$H$_5$ | ½ Ba | [188–189] dec. |
| 80 | —COCH$_3$ | —C$_3$H$_7$ | —CH$_2$CH=CH$_2$ | Na | [163–167] |
| 81 | —CHO | —C$_2$H$_5$ | —C$_2$H$_5$ | Na | [165–170] dec. |
| 82 | 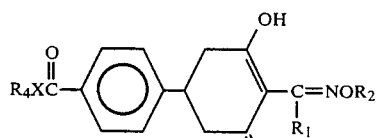 | —C$_2$H$_5$ | —C$_2$H$_5$ | Na | [177] dec. |
| 83 | —COOCH$_3$ | —C$_2$H$_5$ | —C$_2$H$_5$ | Na | [62–65] |
| 84 | —COOC$_2$H$_5$ | —C$_3$H$_7$ | —C$_2$H$_5$ | Na | [170] dec. |
| 85 | —COCF$_3$ | —C$_2$H$_5$ | —C$_2$H$_5$ | Na | [186–188] dec. |
| 86 | —COCF$_3$ | —C$_2$H$_5$ | —CH$_2$CH=CH$_2$ | Na | [181] dec. |

1-5

$$R_4X\overset{O}{\underset{}{\|}}C\!\!-\!\!\bigcirc\!\!-\!\!\underset{\underset{O}{\|}}{\overset{\overset{OH}{|}}{\bigcirc}}\!\!-\!\!\overset{R_1}{\underset{}{C}}\!\!=\!\!NOR_2$$

| Compound No. | R$_4$ | X | R$_1$ | R$_2$ | Physical constant [m.p.] °C. |
|---|---|---|---|---|---|
| 87 | H | O | —C$_2$H$_5$ | —C$_2$H$_5$ | [178–179] |
| 88 | —CH$_3$ | O | —C$_2$H$_5$ | —C$_2$H$_5$ | [75–76] |
| 89 | —CH$_3$ | S | —C$_2$H$_5$ | —C$_2$H$_5$ | [98–100] |

TABLE 1-continued

| | | | | | |
|---|---|---|---|---|---|
| 90 | —CH$_3$ | S | —C$_2$H$_5$ | —CH$_3$ | [110–111] |
| 91 | —CH$_3$ | S | —C$_2$H$_5$ | —CH$_2$CH=CH$_2$ | [87–89] |
| 92 | —CH$_3$ | S | —C$_3$H$_7{}^n$ | —C$_2$H$_5$ | [75–77] |
| 93 | —CH$_3$ | S | —C$_3$H$_7{}^n$ | —CH$_2$C≡CH | [95–96] |
| 94 | —CH$_3$ | S | —C$_3$H$_7{}^n$ | —CH$_2$CH=CH$_2$ | [81–82] |
| 95 | —CH$_3$ | O | —C$_3$H$_7{}^n$ | —C$_2$H$_5$ | [47–49] |
| 96 | —CH$_3$ | O | —C$_3$H$_7{}^n$ | —CH$_2$CH=CH$_2$ | [54–56] |
| 97 | —CH$_3$ | O | —C$_3$H$_7{}^n$ | —CH$_2$C≡CH | [81–83] |
| 98 | —C$_2$H$_5$ | O | —C$_2$H$_5$ | —C$_2$H$_5$ | [77–78] |
| 99 | —C$_2$H$_5$ | O | —C$_2$H$_5$ | —CH$_2$CH=CH$_2$ | [53–54] |
| 100 | C$_2$H$_5$ | O | C$_2$H$_5$ | CH$_3$ | [113–115] |
| 101 | C$_2$H$_5$ | O | C$_3$H$_7{}^n$ | C$_2$H$_5$ | [46–48] |
| 102 | C$_2$H$_5$ | O | C$_3$H$_7{}^n$ | CH$_2$CH=CH$_2$ | [54–56] |
| 103 | C$_2$H$_5$ | S | C$_2$H$_5$ | C$_2$H$_5$ | [88–90] |
| 104 | C$_2$H$_5$ | S | C$_2$H$_5$ | CH$_2$CH=CH$_2$ | [58–60] |
| 105 | C$_2$H$_5$ | S | C$_2$H$_5$ | CH$_3$ | [109–110] |
| 106 | C$_2$H$_5$ | S | C$_3$H$_7{}^n$ | C$_2$H$_5$ | [60–61] |
| 107 | C$_2$H$_5$ | S | C$_3$H$_7{}^n$ | CH$_2$CH=CH$_2$ | [72–75] |
| 108 | CH(CH$_3$)$_2$ | O | C$_2$H$_5$ | C$_2$H$_5$ | [65–67] |
| 109 | —CH(CH$_3$)$_2$ | S | —C$_2$H$_5$ | —C$_2$H$_5$ | [69–71] |
| 110 | —C$_3$H$_7{}^n$ | S | —C$_2$H$_5$ | —C$_2$H$_5$ | [78–80] |
| 111 | —C$_4$H$_9{}^n$ | O | —C$_2$H$_5$ | —C$_2$H$_5$ | [61–62] |
| 112 | —C$_4$H$_9{}^n$ | S | —C$_2$H$_5$ | —C$_2$H$_5$ | [61–62] |
| 113 | —C$_2$CH(CH$_3$)$_2$ | S | —C$_2$H$_5$ | —C$_2$H$_5$ | [45–46] |
| 114 | 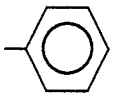 | O | —C$_2$H$_5$ | —C$_2$H$_5$ | [112–114] |
| 115 | 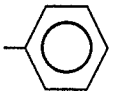 | S | —C$_2$H$_5$ | —C$_2$H$_5$ | [127–128] |
| 116 | 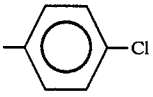 | S | —C$_2$H$_5$ | —C$_2$H$_5$ | [132–134] |
| 117 | H | O | —C$_2$H$_5$ | —C$_2$H$_5$ | 2 Na salt [230–233] dec. |
| 118 | —CH$_3$ | O | —C$_2$H$_5$ | —C$_2$H$_5$ | Na salt [200] up |

1-6

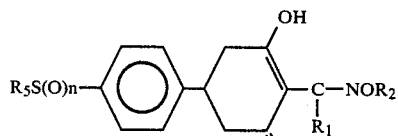

| Compound No. | R$_5$ | n | R$_1$ | R$_2$ | Physical constant [m.p.] °C. |
|---|---|---|---|---|---|
| 119 | —CH$_3$ | 0 | C$_2$H$_5$ | C$_2$H$_5$ | [83–84] |
| 120 | —CH$_3$ | 0 | C$_2$H$_5$ | CH$_2$CH=CH$_2$ | n$_D{}^{20}$ 1.6026 |
| 121 | —CH$_3$ | 1 | C$_2$H$_5$ | C$_2$H$_5$ | [107–109] |
| 122 | —CH$_3$ | 1 | C$_2$H$_5$ | CH$_2$CH=CH$_2$ | n$_D{}^{23}$ 1.5900 |
| 123 | —CH$_3$ | 0 | C$_3$H$_7$ | C$_2$H$_5$ | [82–85] |
| 124 | —CH$_3$ | 0 | C$_3$H$_7$ | CH$_2$CH=CH$_2$ | [72–74] |
| 125 | —CH$_3$ | 1 | C$_3$H$_7$ | C$_2$H$_5$ | [72–74] |
| 126 | —CH$_3$ | 1 | C$_3$H$_7$ | CH$_2$CH=CH$_2$ | n$_D{}^{22}$ 1.5862 |
| 127 | —CH$_3$ | 0 | C$_2$H$_5$ | C$_2$H$_5$ (Na salt) | |
| 128 | —CH$_3$ | 0 | C$_2$H$_5$ | CH$_2$CH=CHCl | n$_D{}^{24}$ 1.5998 |
| 129 | —CH$_3$ | 0 | C$_3$H$_7$ | CH$_2$CH=CHCl | n$_D{}^{24}$ 1.5972 |
| 130 | —CH$_3$ | 0 | C$_2$H$_5$ | CH$_2$CH=CHCl (trans form) | [57–59] |
| 131 | —CH$_3$ | 0 | C$_3$H$_7$ | C$_3$H$_7$ | [80–81] |
| 132 | —CH$_3$ | 0 | C$_3$H$_7$ | CH$_3$ | [60–61] |
| 133 | —C$_2$H$_5$ | 0 | C$_2$H$_5$ | C$_2$H$_5$ | [77–78] |
| 134 | —C$_2$H$_5$ | 1 | C$_2$H$_5$ | C$_2$H$_5$ | [89–90] |
| 135 | —C$_3$H$_7$ | 0 | C$_2$H$_5$ | C$_2$H$_5$ | [63–64] |

As mentioned previously, the compounds possess superior herbicidal activity. The compounds may be applied directly to the soil as pre-emergence treatment or to plant foliage as post-emergence treatment, or they can be mixed intimately with soil. The preferred treatment is post-emergence treatment and the compounds may be applied to soil or to plant foliage in amount of 5 g or more per 10 are.

A herbicidal composition having a compound of this invention as its active ingredient may be formulated by mixing suitable carriers in a form generally used in agricultural chemicals, such as wettable powder, water soluble powder, emulsifiable concentrate and flowable. As solid carriers, talc, white carbon, bentonite, clay, diatomaceous earth or the like may be used. As liquid carriers, water, alcohol, benzene, xylene, kerosene, mineral oil, cyclohexane, cyclohexanone, dimethylformamide or the like may be used. A surface active agent may, if necessary, be added in order to give a homogeneous and stable formulation.

Compounds can also be applied admixed with other chemicals, which are used in agronomic and horticultural management and which are compatible with such compounds. Such chemicals can be, but are not restricted to, the classes of chemical commonly known as fungicides, insecticides, acaricides, herbicides and plant growth regulators. In particular, by mixing it with the other herbicides, its using chemical amount and manpower can be decreased and furthermore, the higher effect of synergetic function with both chemicals can be expected.

For admixture of the compound with known herbicides, the use is recommended of triazine derivatives such as simazine, atrazine and terbutryne, urea derivatives such as ipuron and tribunyl, heterocyclic compounds such as bentazone, phenoxyalkane carboxilic acid derivatives such as 2,4-D and MCPP, benzonirile derivatives such as ioxynil, and sulfoneamide derivatives such as chlorosulfuron.

The concentration of the active ingredient in a herbicidal composition may vary according to type of formulation, and the concentration is, for example, in the range of 5-80 weight percent, preferably 30-60 weight percent, in wettable powder; 70-95 weight percent, preferably 80-90 weight percent, in water soluble powder; 5-70 weight percent, preferably 20-40 weight percent, in emulsifiable concentrate; 10-70 weight percent, preferably 20-50 weight percent, in flowable.

A wettable powder, a water soluble powder or an emulsifiable concentrate thus produced may be diluted with water to a specified concentration and used as a liquid suspension or a liquid emulsion for treating soils or plant foliage. Further, a flowable may be directly used for soil or foliage treatment, otherwise, it may be diluted with water to a specified concentration and used as a liquid suspension for treating soils or plant foliage.

Non-limiting examples of herbicidal composition are illustrated by the following tests:

EXAMPLE 22: Wettable powder

|  | parts by weight |
| --- | --- |
| Compound No. 1 | 50 |
| White carbon | 12 |
| Diatomaceous earth | 30 |
| Sodium alkylsulfate | 8 |

These are mixed homogeneously and reduced to fine particles to provide a wettable powder containing 50% of active ingredient. In use, it is diluted to a desired concentration with water, and is sprayed as suspension.

EXAMPLE 23: Water soluble powder

|  | parts by weight |
| --- | --- |
| Compound No. 118 | 90 |
| Dialkylsulfosuccinate | 10 |

These are mixed homogeneously and reduced to fine particles to provide a water soluble powder containing 90% of active ingredient.

EXAMPLE 24: Emulsifiable concentrate

|  | parts by weight |
| --- | --- |
| Compound No. 120 | 20 |
| Xylene | 40 |
| Dimethylformamide | 30 |
| Polyoxyethylene phenyl ether | 10 |

These are mixed and dissolved to provide an emulsifiable concentrate containing 20% of active ingredient. In use, it is diluted to a desired concentration with water, and sprayed as an emulsion.

EXAMPLE 25: Flowable

|  | parts by weight |
| --- | --- |
| Compound No. 82 | 30 |
| Sun spray-7N (commercial product of Sun Oil Co., Ltd.) | 60 |
| Polyoxyethylene alkylether | 5 |
| Sorbitan alkylate | 5 |

These are mixed homogeneously to provide a flowable containing 30% of active ingredient.

The herbicidal effects of compounds are illustrated by the following tests:

Test 1

Seeds of wild oat and corn were planted in each pot having a surface area of 100 cm$^2$ and kept in a green house. When the plants were grown to 2-2.5 leaves and 2-3 leaves stage respectively, aqueous suspensions, prepared by diluting an emulsifiable concentrate with water to specified concentration containing 400 ppm and 200 ppm of active ingredient were sprayed on the foliage of the test plants at a rate of 100 l/10 are, and the pots were kept in a green house. Twenty eight days after spraying, the degree of damage to each plant was observed and evaluated on the scale of value of 0-10, which has the following meanings:

| Degree of Damage | |
| --- | --- |
| 0 | 0% |
| 2 | 20-29% |
| 4 | 40-49% |
| 6 | 60-69% |
| 8 | 80-89% |
| 10 | 100% |

1, 3, 5, 7 and 9 mean the intermediate degree between 0 and 2, 2 and 4, 4 and 6, 6 and 8, and 8 and 10 respectively.

The results are shown in Table 2.

TABLE 2

| Compound No. | Application Rate (g/10 are) | Degree of Damage wild oat | Degree of Damage corn |
|---|---|---|---|
| 1 | 40 | 10 | 2 |
|   | 20 | 10 | 1 |
| 2 | 40 | 10 | 2 |
|   | 20 | 10 | 1 |
| 3 | 40 | 10 | 3 |
|   | 20 | 10 | 1 |
| 4 | 40 | 10 | 3 |
|   | 20 | 10 | 1 |
| 5 | 40 | 10 | 2 |
|   | 20 | 10 | 0 |
| 6 | 40 | 10 | 3 |
|   | 20 | 10 | 1 |
| 7 | 40 | 9 | 4 |
|   | 20 | 8 | 1 |
| 8 | 40 | 10 | 4 |
|   | 20 | 10 | 2 |
| 9 | 40 | 10 | 4 |
|   | 20 | 10 | 1 |
| 10 | 40 | 10 | 4 |
|    | 20 | 8 | 0 |
| 11 | 40 | 10 | 4 |
|    | 20 | 8 | 0 |
| 12 | 40 | 10 | 3 |
|    | 20 | 7 | 1 |
| 13 | 40 | 10 | 4 |
|    | 20 | 9 | 2 |
| 14 | 40 | 10 | 4 |
|    | 20 | 8 | 2 |
| 15 | 40 | 10 | 3 |
|    | 20 | 9 | 1 |
| 17 | 40 | 10 | 1 |
|    | 20 | 5 | 0 |
| 18 | 40 | 9 | 0 |
|    | 20 | 6 | 0 |
| 19 | 40 | 10 | 2 |
|    | 20 | 9 | 0 |
| 20 | 40 | 9 | 1 |
|    | 20 | 7 | 0 |
| 21 | 40 | 10 | 3 |
|    | 20 | 7 | 1 |
| 22 | 40 | 10 | 3 |
|    | 20 | 6 | 0 |
| 23 | 40 | 10 | 1 |
|    | 20 | 9 | 0 |
| 24 | 40 | 9 | 1 |
|    | 20 | 8 | 1 |
| 25 | 40 | 8 | 2 |
|    | 20 | 7 | 0 |
| 26 | 40 | 10 | 4 |
|    | 20 | 10 | 1 |
| 27 | 40 | 10 | 3 |
|    | 20 | 8 | 0 |
| 28 | 40 | 10 | 2 |
|    | 20 | 9 | 1 |
| 30 | 40 | 10 | 0 |
|    | 20 | 7 | 0 |
| 31 | 40 | 9 | 4 |
|    | 20 | 7 | 3 |
| 32 | 40 | 10 | 3 |
|    | 20 | 7 | 2 |
| 34 | 40 | 10 | 2 |
|    | 20 | 6 | 0 |
| 35 | 40 | 9 | 1 |
|    | 20 | 4 | 0 |
| 36 | 40 | 10 | 2 |
|    | 20 | 6 | 0 |
| 37 | 40 | 9 | 1 |
|    | 20 | 4 | 0 |
| 38 | 40 | 10 | 5 |
|    | 20 | 8 | 2 |
| 39 | 40 | 10 | 4 |
|    | 20 | 8 | 1 |
| 40 | 40 | 8 | 2 |
|    | 20 | 7 | 0 |
| 41 | 40 | 9 | 3 |
|    | 20 | 7 | 1 |
| 42 | 40 | 9 | 1 |
|    | 20 | 7 | 0 |
| 43 | 40 | 9 | 3 |
| 44 | 40 | 10 | 2 |
|    | 20 | 9 | 0 |
| 45 | 40 | 10 | 3 |
|    | 20 | 9 | 0 |
| 46 | 40 | 10 | 4 |
|    | 20 | 10 | 3 |
| 47 | 40 | 10 | 3 |
|    | 20 | 7 | 1 |
| 49 | 40 | 9 | 5 |
|    | 20 | 8 | 2 |
| 50 | 40 | 10 | 4 |
|    | 20 | 9 | 1 |
| 51 | 40 | 10 | 3 |
|    | 20 | 7 | 0 |
| 52 | 40 | 9 | 1 |
|    | 20 | 7 | 0 |
| 60 | 40 | 10 | 2 |
|    | 20 | 8 | 1 |
| 62 | 40 | 9 | 4 |
|    | 20 | 9 | 3 |
| 63 | 40 | 10 | 3 |
|    | 20 | 9 | 2 |
| 64 | 40 | 10 | 2 |
|    | 20 | 8 | 1 |
| 65 | 40 | 9 | 3 |
|    | 20 | 9 | 0 |
| 67 | 40 | 10 | 2 |
|    | 20 | 10 | 1 |
| 68 | 40 | 10 | 2 |
|    | 20 | 10 | 1 |
| 69 | 40 | 9 | 1 |
|    | 20 | 7 | 0 |
| 70 | 40 | 9 | 0 |
|    | 20 | 6 | 0 |
| 71 | 40 | 9 | 1 |
|    | 20 | 6 | 0 |
| 72 | 40 | 8 | 1 |
|    | 20 | 6 | 0 |
| 73 | 40 | 10 | 3 |
|    | 20 | 10 | 2 |
| 74 | 40 | 10 | 4 |
|    | 20 | 10 | 1 |
| 75 | 40 | 10 | 4 |
|    | 20 | 10 | 2 |
| 76 | 40 | 10 | 3 |
|    | 20 | 10 | 2 |
| 77 | 40 | 10 | 2 |
|    | 20 | 8 | 1 |
| 78 | 40 | 10 | 3 |
|    | 20 | 9 | 1 |
| 79 | 40 | 9 | 1 |
|    | 20 | 7 | 0 |
| 80 | 40 | 10 | 4 |
|    | 20 | 9 | 1 |
| 81 | 40 | 9 | 3 |
|    | 20 | 7 | 0 |
| 82 | 40 | 10 | 4 |
|    | 20 | 8 | 2 |
| 83 | 40 | 10 | 3 |
|    | 20 | 8 | 0 |
| 84 | 40 | 10 | 2 |
|    | 20 | 8 | 0 |
| Comparative compound A | 40 | 9 | 10 |
|    | 20 | 7 | 7 |
| Comparative compound B | 40 | 10 | 10 |
|    | 20 | 8 | 7 |

Comparative Compound A:
2-[1-(ethoxyimino)propyl]-3-hydroxy-5-phenyl-2-cyclohexen-1-one B: 2-[1-(ethoxyimino)propyl]-3-hydroxy-5-(4-methoxyphenyl)-2-cyclohexen-1-one Test 2

Seeds of wild oat and wheat were planted in each pot having a surface area of 100 cm² and kept in a green house. When the plants were grown to 2–3 leaves stage respectively, aqueous suspensions, prepared by diluting an emulsifiable concentrate, with water to specified concentration containing 400 ppm and 200 ppm of active ingredient were sprayed on the foliage of the test plants at a rate of 100 1/10 are, and the pots were kept in a green house. Twenty eight days after spraying, the degree of damage to each plant was observed and evaluated on the same scale in Test 1.

The results are shown in Table 3.

TABLE 3

| Compound No. | Application Rate (g/10 are) | Degree of Damage wild oat | wheat |
|---|---|---|---|
| 87 | 40 | 10 | 0 |
|  | 20 | 5 | 0 |
| 88 | 40 | 10 | 0 |
|  | 20 | 8 | 0 |
| 89 | 40 | 10 | 1 |
|  | 20 | 10 | 0 |
| 91 | 40 | 9 | 0 |
|  | 20 | 6 | 0 |
| 92 | 40 | 10 | 0 |
|  | 20 | 10 | 0 |
| 93 | 40 | 9 | 0 |
|  | 20 | 5 | 0 |
| 94 | 40 | 10 | 2 |
|  | 20 | 10 | 0 |
| 95 | 40 | 10 | 0 |
|  | 20 | 8 | 0 |
| 96 | 40 | 10 | 0 |
|  | 20 | 10 | 0 |
| 97 | 40 | 9 | 0 |
|  | 20 | 3 | 0 |
| 98 | 40 | 10 | 0 |
|  | 20 | 7 | 0 |
| 99 | 40 | 10 | 1 |
|  | 20 | 5 | 0 |
| 101 | 40 | 10 | 0 |
|  | 20 | 10 | 0 |
| 102 | 40 | 10 | 1 |
|  | 20 | 10 | 0 |
| 103 | 40 | 10 | 0 |
|  | 20 | 7 | 0 |
| 104 | 40 | 10 | 2 |
|  | 20 | 10 | 0 |
| 106 | 40 | 10 | 0 |
|  | 20 | 10 | 0 |
| 107 | 40 | 10 | 1 |
|  | 20 | 10 | 0 |
| 108 | 40 | 10 | 0 |
|  | 20 | 10 | 0 |
| 109 | 40 | 9 | 0 |
|  | 20 | 6 | 0 |
| 110 | 40 | 10 | 0 |
|  | 20 | 7 | 0 |
| 111 | 40 | 9 | 0 |
|  | 20 | 7 | 0 |
| 112 | 40 | 5 | 0 |
|  | 20 | 4 | 0 |
| 114 | 40 | 8 | 0 |
|  | 20 | 6 | 0 |
| 117 | 40 | 10 | 0 |
|  | 20 | 4 | 0 |
| 118 | 40 | 10 | 0 |
|  | 20 | 8 | 0 |
| Comparative compound C | 40 | 10 | 4 |
|  | 20 | 6 | 0 |
| Comparative compound A | 40 | 9 | 5 |
|  | 20 | 4 | 3 |

Comparative compound C:
2-[1-(ethoxyimino)propyl]-3-hydroxy-5-(4-methylphenyl)-2-cyclohexen-1-one
A: The same in Test 1.

Test 3

Seeds of wild oat and wheat were planted in each pot having a surface area of 100 cm² and kept in a green house. When the plants were grown to 3–4 leaves stage respectively, aqueous suspensions, prepared by diluting an emulsifiable concentrate with water to specified concentration containing 400 ppm and 200 ppm of active ingredient were sprayed on the foliage of the test plants at a rate of 100 1/10 are, and the pots were kept in a green house. Twenty eight days after spraying, the degree of damage to each plant was observed and evaluated on the same scale in Test 1.

The results are shown in Table 4.

TABLE 4

| Compound No. | Application Rate (g/10 are) | Degree of Damage wild oat | wheat |
|---|---|---|---|
| 119 | 40 | 10 | 5 |
|  | 20 | 10 | 2 |
| 120 | 40 | 10 | 4 |
|  | 20 | 10 | 2 |
| 121 | 40 | 10 | 2 |
|  | 20 | 10 | 2 |
| 122 | 40 | 10 | 4 |
|  | 20 | 10 | 2 |
| 123 | 40 | 10 | 3 |
|  | 20 | 10 | 2 |
| 124 | 40 | 10 | 3 |
|  | 20 | 10 | 4 |
| 125 | 40 | 10 | 2 |
|  | 20 | 10 | 2 |
| 126 | 40 | 10 | 5 |
|  | 20 | 10 | 4 |
| 127 | 40 | 10 | 5 |
|  | 20 | 10 | 2 |
| 131 | 40 | 10 | 3 |
|  | 20 | 10 | 2 |
| 132 | 40 | 10 | 3 |
|  | 20 | 10 | 2 |
| 133 | 40 | 10 | 4 |
|  | 20 | 10 | 3 |
| 134 | 40 | 10 | 5 |
|  | 20 | 10 | 2 |
| 135 | 40 | 10 | 3 |
|  | 20 | 10 | 3 |
| Comparative compound D | 40 | 10 | 3 |
|  | 20 | 8 | 5 |
| Comparative compound B | 40 | 9 | 5 |
|  | 20 | 6 | 2 |
| Comparative compound C | 40 | 9 | 2 |
|  | 20 | 5 | 3 |

Comparative compound D:
2-[1-(ethoxyimino)propyl]-3-hydroxy-5-(4-methanesulfonylphenyl)-2-cyclohexen-1-one
B: The same in Test 1
C: The same in Test 2

Test 4

Seeds of wild oat, crabgrass, wheat and barley were planted in each pot having a surface area of 100 cm² kept in a green house. When the wild oat and crabgrass were grown to the tillering stage (20–30 cm of shoot length) and wheat and barley were grown to the stage of 30–35 cm of shoot length respectively, aqueous suspensions, prepared by diluting a wettable powder with water to specified concentration containing 750 ppm, 500 ppm, 250 ppm and 125 ppm of active ingredient were sprayed on the foliage of the test plants at a rate of 100 1/10 are, and the pots were kept in a green house. Twenty eight days after spraying, the degree of damage to each plant was observed and evaluated on the same scale in Test 1.

The results are shown in Table 5.

TABLE 5

| Compound No. | Application Rate (g/10 are) | Degree of Damage | | | |
|---|---|---|---|---|---|
| | | wild oat | crabgrass | wheat | barley |
| 119 | 75 | 10 | 10 | 5 | 5 |
| | 50 | 10 | 10 | 2 | 3 |
| | 25 | 10 | 10 | 1 | 1 |
| | 12.5 | 9 | 7 | 0 | 0 |
| 121 | 75 | 10 | 10 | 4 | 5 |
| | 50 | 10 | 10 | 3 | 2 |
| | 25 | 10 | 10 | 1 | 2 |
| | 12.5 | 6 | 4 | 0 | 0 |
| 123 | 75 | 10 | 10 | 5 | 4 |
| | 50 | 10 | 10 | 3 | 2 |
| | 25 | 10 | 10 | 2 | 1 |
| | 12.5 | 6 | 5 | 0 | 0 |
| Comparative compound C | 75 | 10 | 8 | 3 | 4 |
| | 50 | 9 | 6 | 3 | 3 |
| | 25 | 5 | 4 | 1 | 1 |
| | 12.5 | 4 | 1 | 0 | 0 |

Comparative compound C:
The same in Test 2.
What we claim is:
1. A compound of the formula

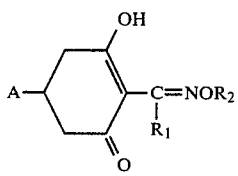

wherein
$R_1$ is alkyl having 1-3 carbon atoms;
$R_2$ is alkyl having 1-3 carbon atoms, allyl, propargyl or haloalkenyl; and
A is selected from the group consisting of a

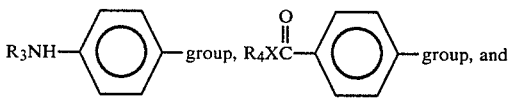

wherein $R_3$ is —$SO_2R_6$ group,

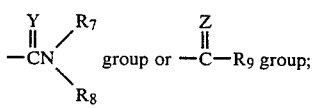

$R_4$ is hydrogen, alkyl having 1-6 carbon atoms, phenyl or halophenyl; $R_5$ is alkyl having 1-3 carbon atoms; X is oxygen or sulfur; and n is 0 or 1; wherein $R_6$ is alkyl having 1-6 carbon atoms, haloalkyl having 1-6 carbon atoms or propenyl; $R_7$ is hydrogen or alkyl having 1-4 carbon atoms, $R_8$ is hydrogen, alkyl having 1-6 carbon atoms, propenyl or methoxy; $R_9$ is hydrogen, alkyl having 1-8 carbon atoms, haloalkyl having 1-3 carbon atoms, alkoxy having 1-6 carbon atoms, propenyl or phenyl substituted with methyl; and Y and Z are oxygen or sulfur;

and a metal salt or a quaternary ammonium salt of a compound defined herein above.

2. A compound according to claim 1, wherein A is a

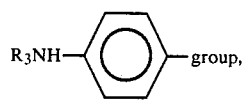

and $R_3$ has the meaning set forth in claim 1.

3. A compound according to claim 2 wherein $R_3$ is a —$SO_2R_6$ group and $R_6$ has the meaning set forth in claim 1.

4. A compound according to claim 2 wherein $R_3$ is a

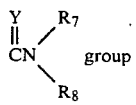

and $R_7$ and $R_8$ have the meaning set forth in claim 1.

5. A compound according to claim 2, wherein $R_3$ is a

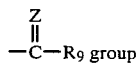

and $R_9$ has the meaning set forth in claim 1.

6. A compound according to claim 1, wherein A is a

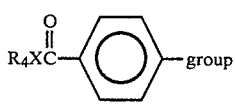

and $R_4$ and X have the meaning set forth in claim 1.

7. A compound according to claim 1 wherein A is a

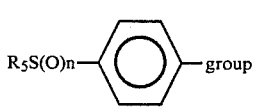

and $R_5$ and n have the meaning set forth in claim 1.

8. A herbicidal composition comprising an inert carrier and an effective amount of a compound of claim 1.

9. A herbicidal composition comprising an inert carrier and an effective amount of a compound of claim 2.

10. A herbicidal composition comprising an inert carrier and an effective amount of a compound of claim 3.

11. A herbicidal composition comprising an inert carrier and an effective amount of a compound of claim 4.

12. A herbicidal composition comprising an inert carrier and an effective amount of a compound of claim 5.

13. A herbicidal composition comprising an inert carrier and an effective amount of a compound of claim 6.

14. A herbicidal composition comprising an inert carrier and an effective amount of a compound of claim 7.

15. A process for the preparation of a compound of the formula

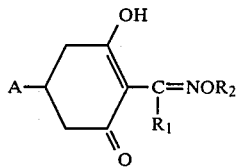

which comprises reacting a compound of the formula

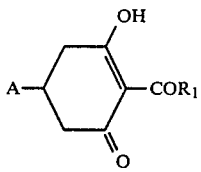

with a compound of the formula

R₂ONH₂ wherein
R₁ is alkyl having 1-3 carbon atoms;
R₂ is alkyl having 1-3 carbon atoms, allyl, propargyl or haloalkenyl; and A is selected from the group consisting of

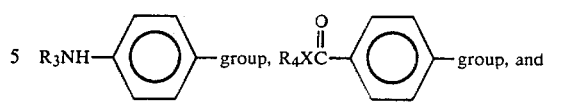

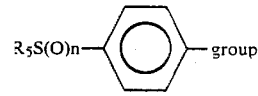

wherein R₃ is —SO₂R₆ group,

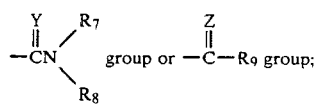

$R_4$ is hydrogen, alkyl having 1-6 carbon atoms, phenyl or halophenyl; $R_5$ is alkyl having 1-3 carbon atoms; X is oxygen or sulfur; and n is 0 or 1; wherein $R_6$ is alkyl having 1-6 carbon atoms, haloalkyl having 1-6 carbon atoms or propenyl; $R_7$ is hydrogen or alkyl having 1-4 carbon atoms; $R_8$ is hydrogen, alkyl having 1-6 carbon atoms, propenyl or methoxy; $R_9$ is hydrogen having 1-8 carbon atoms, haloalkyl having 1-3 carbon atoms, alkoxy having 1-6 carbon atoms, propenyl or phenyl substituted with methyl; and Y and Z are oxygen or sulfur.

* * * * *